United States Patent
Root et al.

(10) Patent No.: US 6,235,044 B1
(45) Date of Patent: May 22, 2001

(54) PERCUTANEOUS CATHETER AND GUIDEWIRE FOR FILTERING DURING ABLATION OF MYCARDIAL OR VASCULAR TISSUE

(75) Inventors: Jonathan D. Root, San Francisco, CA (US); Kevin Hahnen, Sarasota, FL (US); Tracy D. Maahs, Santa Clara, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/369,060

(22) Filed: Aug. 4, 1999

(51) Int. Cl.[7] ................................................. A61B 17/22
(52) U.S. Cl. ............................................................ 606/200
(58) Field of Search ................................. 606/200, 194, 606/108, 41, 45, 127; 604/96, 104–106

(56) References Cited

U.S. PATENT DOCUMENTS

| 5,662,671 | 9/1997 | Barbut et al. ......................... 606/170 |
| 5,800,457 | * 9/1998 | Gelfish .................................. 606/200 |
| 5,827,324 | 10/1998 | Cassell et al. ........................ 606/200 |
| 5,916,193 | * 6/1999 | Stevens et al. .................. 606/194 X |

FOREIGN PATENT DOCUMENTS 0 472 368A2   2/1992  (EP).

OTHER PUBLICATIONS

Haissaguerre et al., "Spontaneous Initiation of Atrial Fibrillation by Ectopic Beats Originating in the Pulmonary Veins," *The New England Journal of Medicine* 339(10):659–666 (Sep. 1998).

Lesh, "Can Catheter Ablation Cure Atrial Fibrillation?" *ACC Current Journal Review*, p. 38, Sep./Oct. 1997.

* cited by examiner

*Primary Examiner*—Michael Buiz
*Assistant Examiner*—(Vikki) Hoa B. Trinh
(74) *Attorney, Agent, or Firm*—Compton, Seager & Tufte, LLC

(57) ABSTRACT

An ablation catheter system for capturing and removing necrotic tissue and thrombi generated during an ablative procedure is disclosed. The catheter typically includes an elongate member, a filtration assembly disposed within the distal region, and an ablation instrument at the distal end. Alternatively, the ablation instrument is carried on the distal end of an ablation catheter, which is disposed within a lumen of the catheter system. The catheter may further include an aspiration port and lumen. Methods of using the devices in preventing distal embolization during ablative procedures are disclosed.

20 Claims, 8 Drawing Sheets

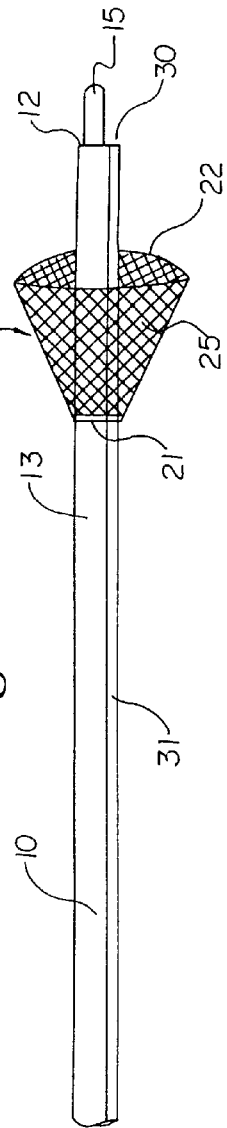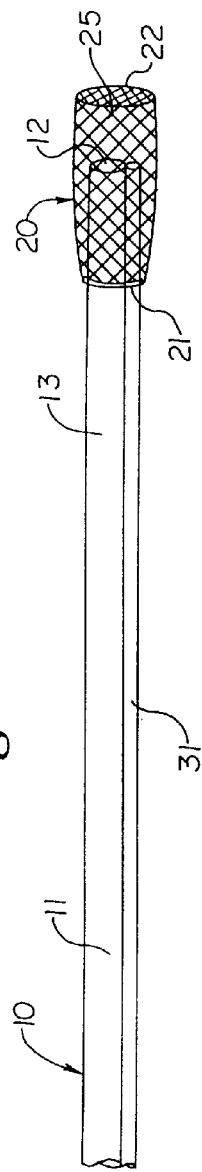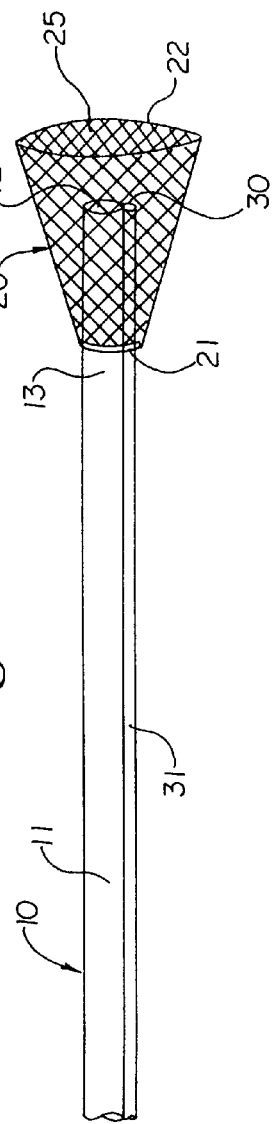

PERCUTANEOUS CATHETER AND GUIDEWIRE FOR FILTERING DURING ABLATION OF MYCARDIAL OR VASCULAR TISSUE

FIELD OF THE INVENTION

The present invention generally relates to devices and methods useful in capturing embolic material during ablation of myocardial or vascular tissue. More specifically, the devices remove necrotic tissue debris generated during ablation of ectopic foci, e.g., in the left atrium, the right atrium, and the pulmonary vein, in patients with paroxysmal atrial fibrillation or other sustained atrial tachyarrhythmias. The devices include a trapping mechanism for capturing the necrotic tissue debris and may include aspiration capabilities.

BACKGROUND OF THE INVENTION

Atrial fibrillation is the most common sustained arrhythmia in the United States, affecting over 2 million people. Its prevalence increases with age up to 5 percent in people more than 65 years of age. Atrial fibrillation is perpetuated by reentrant wavelets propagating outside the normal cardiac conduction pathway, resulting in rapid, irregular heart rate and the loss of atrioventricular synchrony. Atrial fibrillation is also important because of the associated fivefold increase in incidence of stroke.

Three patterns of atrial fibrillation exist: paroxysmal (intermittent), persistent (but able to be cardioverted), and permanent (cardioversion-resistent), with the pattern progressing over time in a given patient. Two strategies generally exist for managing patients with atrial fibrillation: rate control and anticoagulation versus attempts to restore and maintain sinus rhythm. Generally, in most patients, initial attempts are undertaken to restore sinus rhythm with electrical or pharmacologic cardioversion. Standard anti-arrhythmic agents include amiodarone, procainamide, or quinidine. However, disadvantages associated with anti-arrhythmic therapy are that (1) the anti-arrhythmic agents are pro-arrhythmic, e.g., causing torsades de pointe, (2) the anti-arrhythmic agents often carry significant side effects, such as lupus-like syndrome and agranulocytosis, and (3) even with two anti-arrhythmic drugs, some patients may be resistant to pharmacological therapy, e.g., patients may continue to have at least one episode of atrial fibrillation every two days or frequent isolated atrial ectopic beats (more than 700 per day).

If medical therapy fails to convert atrial fibrillation, electrical cardioversion, either externally or via an implanted device, can be attempted using 100 to 200 W•s of energy. Anticoagulation is usually recommended to reduce the incidence of embolization associated with cardioversion. Current recommendations suggest long-term anticoagulation for 3 to 4 weeks before cardioversion and 2 to 4 weeks following cardioversion.

Other treatment options for atrial fibrillation include catheter ablation of the atrioventricular (AV) node with pacemaker implantation, or modification of the AV node without pacemaker implantation. However, thromboembolic risk is unchanged and atrial systole is not restored with these procedures. Several alternatives have also been available to interrupt the reentrant wavelets, including extensive surgical, or recently, catheter-medicated atriotomy. Using the current techniques, the success rate of catheter ablation of other sustained atrial arrhythmias, e.g., atrial flutter and sustained atrial tachycardia, has been over 90%. Catheter ablation therefore represents an important alternative to pharmacologic therapy for treatment of atrial fibrillation and other sustained atrial arrhythmias.

In order to ablate the ectopic foci, electrophysiologic study (EPS) is required to locate the foci responsible for triggering of atrial fibrillation. According to Haissaguerre, et al., The New England Journal of Medicine (1998), vol. 339, No. 10, p. 659–666, incorporated herein by reference in its entirety, three multi-electrode catheters are introduced percutaneously through the femoral veins: one catheter for ablation, one mapping catheter for positioning in the right atrial appendage (for locating ectopic foci in the right atrial and right pulmonary vein) or coronary sinus (for locating ectopic foci in the left pulmonary vein), and another catheter for stimulation of the atrial tissue to induce atrial fibrillation. In this study, patients with paroxysmal atrial fibrillation were found to have ectopic beats originating in the atrial muscle ("atrial foci") and in pulmonary veins (the left superior, left inferior, right superior, and right inferior pulmonary veins). Direct mapping and ablation of the left atrium and pulmonary veins were performed via a transseptal approach through the foramen ovale which lies in the interatrial septum. Alternatively, the catheters may be inserted retrograde in the aorta through the aortic valve and left ventricle. The ablation was performed at the site with earliest recorded ectopic activity.

The ablative techniques used to restore normal sinus rhythm, where the tissue surface is subjected to extreme localized temperature designed to kill cellular structures, can generate necrotic tissue fragments or blood clots. These tissue debris or thrombi may travel downstream from the procedural site to lodge in other organs, causing stroke, myocardial infarction, renal infarcts, and tissue ischemia in other organs. New devices and methods are thus needed for an ablation catheter having an ability to entrap and/or remove embolic debris generated during ablation of ectopic atrial foci in patients with atrial fibrillation or other sustained atrial arrhythmias, thereby reducing the risk of embolization.

SUMMARY OF THE INVENTION

It is known that patients with drug and cardioversion refractory paroxysmal atrial fibrillation and other sustained atrial arrhythmias, e.g., atrial flutter and sustained atrial tachycardia, may benefit from catheter ablation of ectopic atrial foci. The present invention provides devices and methods which include filtering and aspiration capabilities for trapping and removing necrotic tissue debris and thrombi generated during the ablative therapy, thereby minimizing embolization to other organs.

In one embodiment, the medical device comprises a catheter which includes a flexible elongate member having a distal end adapted to enter a vessel and a proximal end which extends from a patient's vessel and permits control outside the patient's body by a physician. At the distal end of the catheter is provided an ablation device and an expandable trapping mechanism. The ablation device may utilize radio frequency, laser, cryogenic, or microwave. The trapping mechanism, in certain embodiments, comprises an open-ended tubular member which extends to the proximal region of the catheter and is attached to a vacuum. In other embodiments, the trapping mechanism comprises a basket or opening in a tube, which is mounted proximal to the ablation device and surrounds the ablation device.

In another embodiment, the catheter may include a filtration mesh, typically disposed circumferentially about a distal region of the catheter proximal to the ablation device, so that filtration occurs downstream of the ablation. The filter will typically include a continuous mesh having a proximal edge circumferentially in contact with the outer surface of the catheter and a distal edge attached to an expansion mechanism, which contracts and expands radially outward. The construction and use of expansion means and associated filter mesh on a cannula have been thoroughly discussed in our earlier applications, including Barbut et al., U.S. Application Serial No., U.S. application Ser. No. 08/553,137, filed Nov. 7, 1995, Barbut et al., U.S. application Ser. No. 08/580,223, filed Dec. 28, 1995, Barbut et al., U.S. application Ser. No. 08/584,759, filed Jan. 9, 1996, Barbut et al., U.S. Pat. No. 5,769,816, and Barbut et al., U.S. application Ser. No. 08/645,762, filed May 14, 1996, Barbut et al., U.S. Pat. No. 5,662,671, Maahs, U.S. Pat. No. 5,846,260, and Tsugita et al., U.S. Pat. No. 5,911,734, all of which are incorporated herein by reference in their entirety.

In still another embodiment, the catheter includes a second lumen communicating with a proximal end and an aspiration port at its distal end. The proximal end of the catheter is adapted for attachment to a vacuum. The port is located distal to the trapping mechanism and proximal to the ablation device for removing tissue debris generated during the ablation.

In still another embodiment, the device comprises a flexible elongate tube having a lumen communicating with a proximal end and a distal end. An expandable entrapping mechanism is mounted on a distal region of the catheter. An ablation catheter, which includes an ablation device at its distal end, is disposed within the lumen of the catheter. In certain embodiments, the catheter may include a second lumen communicating with a distal port adapted for aspiration of tissue debris.

The methods of the present invention protect a patient from embolization during ablative procedures to remove ectopic atrial foci in the right atrium, the left atrium, and/or the pulmonary veins. Using the devices described above, the distal end of the catheter is inserted percutaneously through a peripheral vein, e.g., the femoral vein, the brachial vein, the subclavian vein, or the internal/external jugular vein, into the right atrium. To ablate the ectopic foci in the right atrial appendage, the ablation device is positioned adjacent to the foci, and the entrapping mechanism, or filter, is expanded. During the ablation, necrotic tissue particles and/or thrombi generated are captured by the filter and/or removed by aspiration. To ablate the ectopic foci in the left atrial tissue or the pulmonary veins, the distal end of the catheter is advanced from the right atrium, through the foramen ovale, and enters the left atrium. Alternatively, the distal end of the catheter may be inserted percutaneously through a peripheral artery, e.g., the femoral artery, the brachial artery, the subclavian artery, or the axillary artery, retrograde into the aorta, the left ventricle, and the left atrium to access the foci in the left atrium or the pulmonary vein. It will be understood that the devices and methods can also be employed in an open surgical procedure (Maze technique).

In another method, after the ectopic atrial foci are located by electrophysiologic mapping, the distal end of the flexible guiding catheter carrying the filter at its distal region is inserted downstream the site of ablation. The filter is expanded. A steerable ablation catheter, having an ablation device mounted at its distal end, is inserted in the lumen of the guiding catheter to ablate the ectopic foci.

After the embolic tissue debris are entrapped by the filter, the filter is contracted to resume a small shape in close contact with the outer surface of the catheter. The catheter, with captured embolic material, is then withdrawn from the aorta or the vein and removed from the patient's body.

The devices and methods disclosed herein are best used in preventing peripheral embolization during ablation of ectopic foci in the right atrium, the left atrium, and the pulmonary veins in patients with atrial fibrillation or other sustained atrial arrhythmias. It will be understood that the devices and methods are applicable to ablating ectopic tissues in other cardiac arrhythmias, such as ventricular tachycardia or Wolff-Parkinson-White syndrome.

BRIEF DESCRIPTION OF THE DRAWINGS

FIG. 4 depicts another embodiment of the ablation catheter having an aspiration port.

FIG. 6A depicts an embodiment of a guiding catheter system for ablation of ectopic foci having a filtration assembly in a contracted state.

FIG. 6B depicts the embodiment of FIG. 6A having the filtration assembly in an expanded state.

DETAILED DESCRIPTION

Figure 1:
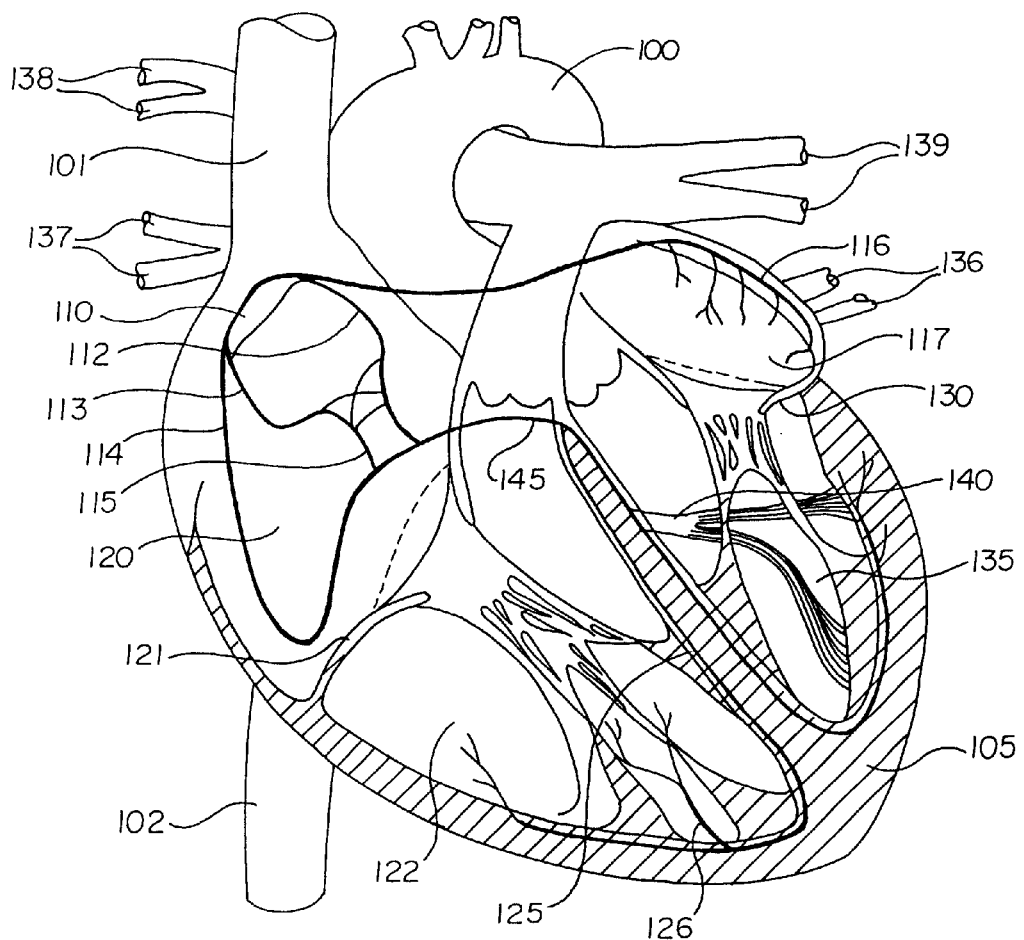
FIG. 1 depicts a normal cardiac conduction pathway.

Normal cardiac conduction originates in sinoatrial (SA) node 110, located in the upper wall of right atrium 120 as depicted in FIG. 1. The SA node, the heart's main pacemaker, generates electrical activity which travels through a conduction pathway. Electrical impulses travel from SA node 110 over Bachmann's bundle 116 to left atrium 117, along anterior internodal tract 112, middle internodal tract 113, and posterior internodal tract 114 in right atrium 120 to atrioventricular (AV) node 115. At the AV node the impulse is delayed for approximately 40 milliseconds, allowing atrial contraction, and resumes down through bundle of His 145. The electrical impulse travels rapidly into right bundle branch 125 and left bundle branch 140 and continues down the interventricular septum. From the bundle branches, the impulse continues through Purkinje fibers, which rapidly conduct the impulse to both ventricular endocardium. In this way, the electrical impulse generated from the SA node and terminating in the Purkinje fibers constitutes a cardiac conduction cycle, triggering atrial and ventricular contraction and relaxation, causing the heart to pump blood. After right atrium 120 receives deoxygenated blood from superior vena cava (SVC) 101 and inferior vena cava (IVC) 102, the blood is passed through tricuspid valves 121 into right ventricle 122. The deoxygenated blood is ejected from the right ventricle into right pulmonary arteries 138 and left pulmonary arteries 139, oxygenated by the lung, and returned to left atrium 117 via right pulmonary veins 137 and left pulmonary veins 136. The oxygenated blood passes through mitral valve 130 into left ventricle 135, which ejects the blood into aorta 100 to perfuse the peripheral organs.

Figure 2A:
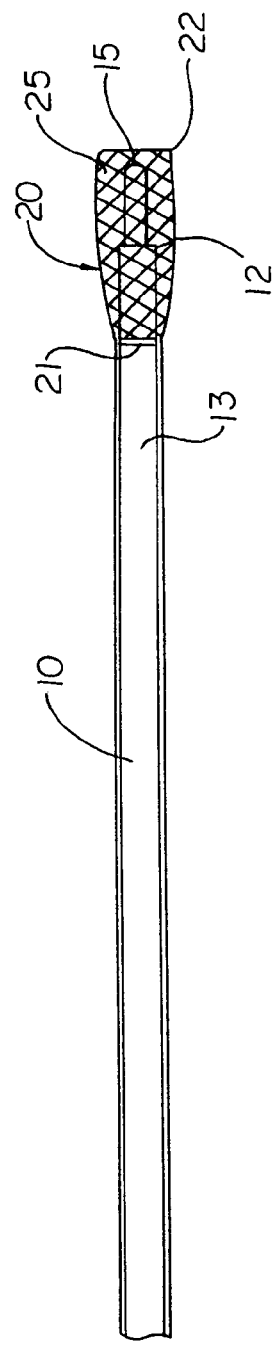
FIG. 2A depicts an embodiment of an ablation catheter having a trapping mechanism for capturing emboli, comprising a filtration assembly in a contracted state.
Figure 2B:
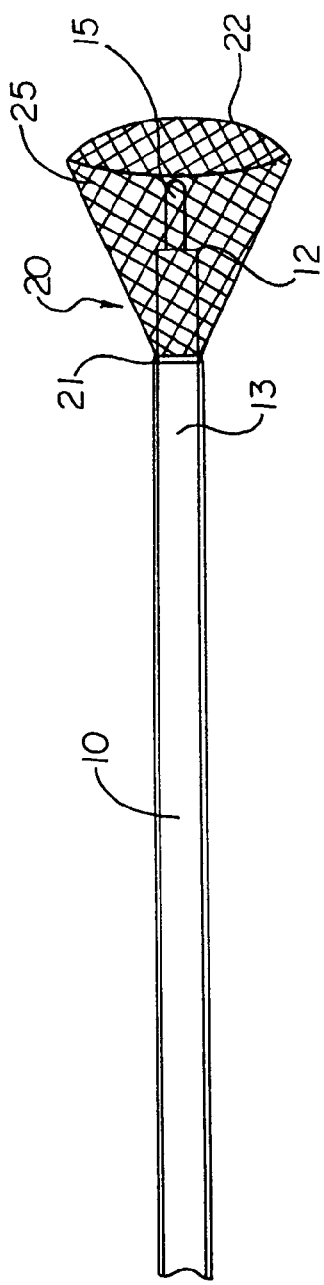
FIG. 2B depicts the catheter of FIG. 2A having the filtration assembly in an expanded state.

An embodiment of an ablation catheter with associated filter is depicted in FIGS. 2A and 2B. The catheter includes a flexible elongate member 10 having a proximal end, distal end 12, ablation instrument 15 mounted at the distal end, and an expansion means, typically filtration assembly 20, mounted on distal region 13 of the catheter. The filtration assembly includes proximal edge 21 circumferentially in contact with an outer surface of the catheter and distal edge 22 which expands radially outward. Filter mesh 25 is associated with the outer surface of the catheter at proximal edge 21 and is operably connected to the filter assembly at distal edge 22. Having the filter assembly in a contracted state as depicted in FIG. 2A facilitates insertion of the catheter into a peripheral vessel, such as the femoral vein or artery. After the distal end of the catheter is positioned in an area of interest, filter assembly 20 is expanded as depicted in FIG. 2B to capture embolic debris. Alternative expansion means based on a mechanical expanding mechanism similar to an umbrella frame are described in U.S. application Ser. Nos. 08/553,137, 08/580,223, 08/584,759, 08/640,015, and 08/645,762, incorporated herein by reference in their entirety.

Figure 3:
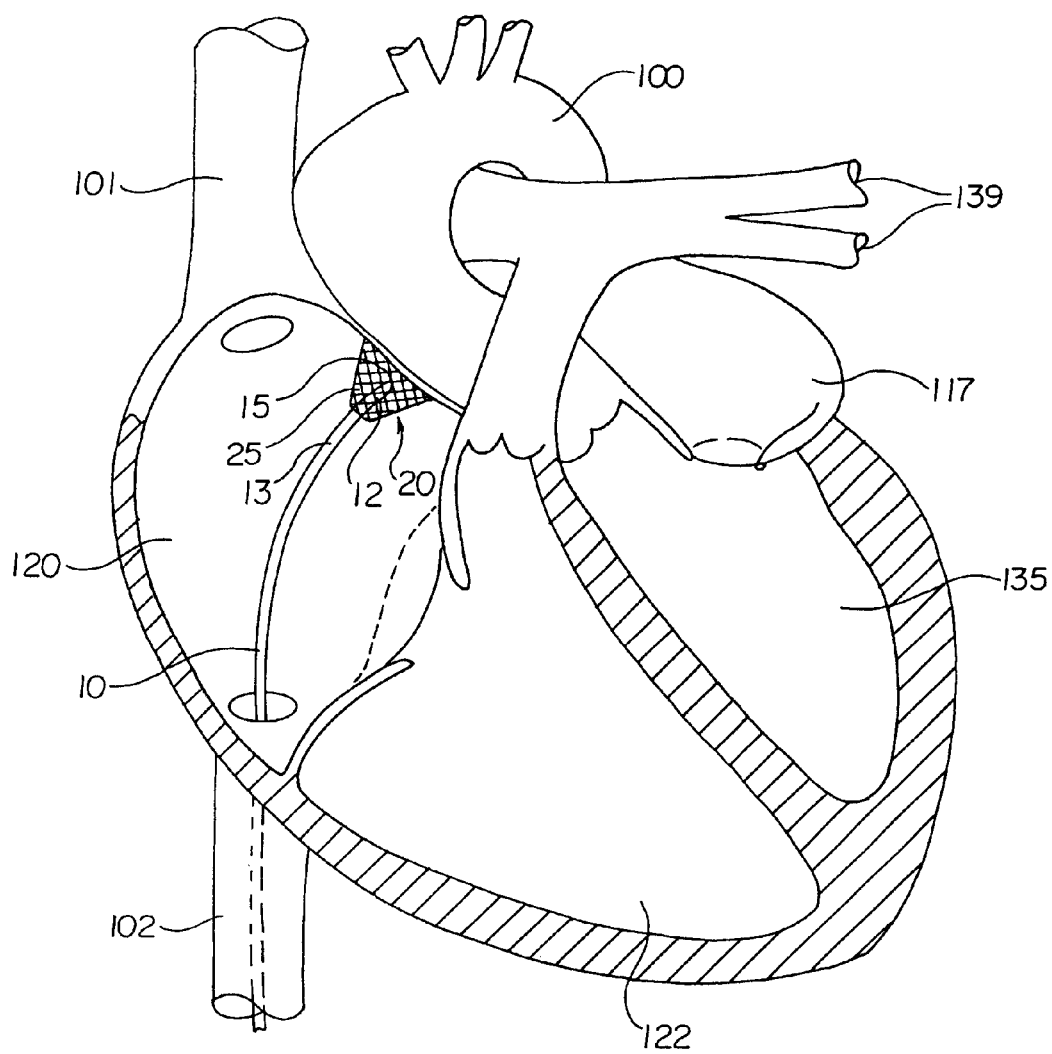
FIG. 3 depicts the ablation catheter of FIG. 2B inserted in the right atrium.

In using the ablation catheter of FIGS. 2A and 2B to ablate ectopic right atrial foci for treatment of atrial fibrillation or other sustained atrial tachycardia, the distal end of the catheter can be inserted through a peripheral vein, e.g., the subclavian vein or the internal jugular vein, and through the superior vena cava to insert into the right atrium. Alternatively, distal end 13 of the catheter is inserted through the femoral artery and up through inferior vena cava 102 into right atrium 120 as depicted in FIG. 3. Filtration assembly 20 is contracted at distal region 13 to facilitate catheter insertion. After ectopic atrial foci are located with EPS, ablation instrument 15 is position adjacent to the affected atrial tissue. Filtration assembly 20 is expanded about distal end 12 of the catheter. The ectopic foci can be ablated using radio frequency, microwave, laser, or cryogenic techniques. Necrotic tissue debris or thrombi generated during the ablation procedure are captured by mesh 25. After the completion of the procedure, filtration assembly is contracted, securing the embolic material in the mesh, and removed when the catheter is withdrawn proximally, preventing distal embolization.

Another embodiment of the ablation catheter having aspiration port 30 communicating with lumen 31 is depicted in FIG. 4. Lumen 31 at its proximal end is adapted for attachment to a vacuum. The aspiration port is capable of removing myocardial tissue debris or thrombi generated during the ablative procedure under suction. In this embodiment, filtration assembly 20 is mounted on distal region 13 of the catheter, proximal to distal end 12 and ablation instrument 15.

Figure 5:
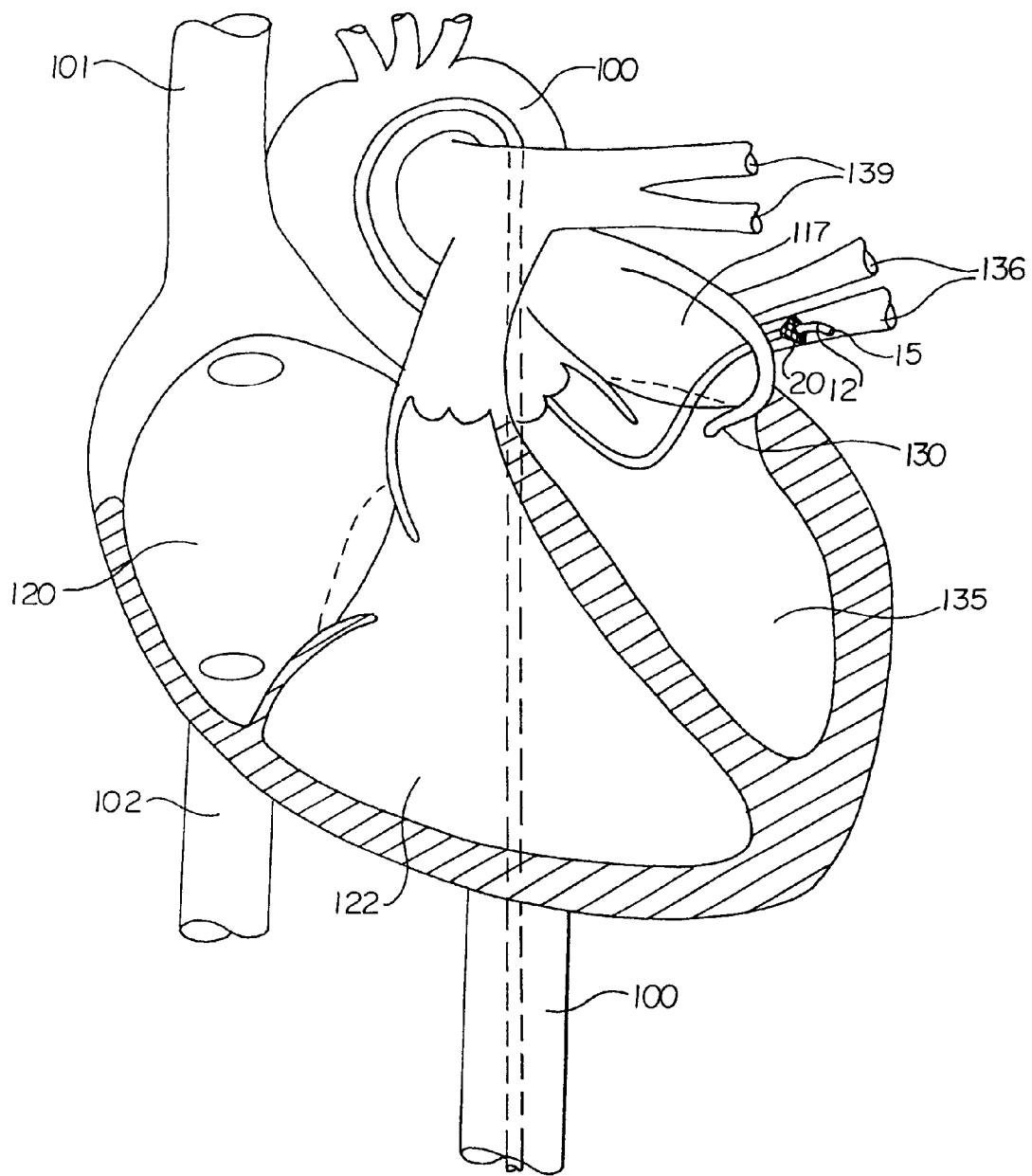
FIG. 5 depicts the device of FIG. 4 inserted in the pulmonary vein.

Using the ablation catheter of FIG. 4 may be preferred for ablation of pulmonary veins. In FIG. 5, distal end 12 of the catheter and the contracted filtration assembly are inserted through a peripheral artery, such as the femoral artery, up through aorta 100, and traverses left ventricle 135, mitral valve 130, and left atrium 117 to insert in left pulmonary vein 136. Alternatively, distal end 12 of the catheter can be inserted through the brachial or the subclavian artery to insert in pulmonary vein 136 via aorta 100 in a retrograde fashion. Alternatively, the catheter can be inserted through a peripheral vein to enter into right atrium 120 via SVC 101 or IVC 102, and insert in pulmonary vein 136 by traversing the foramen ovale, which is patent in some patients, to enter left atrium 117. After ectopic foci are located in the pulmonary vein, ablation assembly 20 is expanded circumferentially to contact the walls of the pulmonary vein. During the ablation of the ectopic foci by ablation instrument 15, necrotic tissue debris and thrombi generated can be aspirated by the aspiration port at distal end 12 of the catheter or can be captured by the expanded filtration assembly. After completion of the ablative procedure, the filtration assembly is contracted and removed with the catheter, thereby preventing the emboli from entering left atrium 117, through mitral valve 130, left ventricle 135, and exiting aorta 100 downstream to lodge in the peripheral organs.

An embodiment of a percutaneous guiding catheter system for ablation of ectopic foci is shown in FIGS. 6A and 6B. The catheter system includes elongate tubular member 10 having lumen 11 communicating with a proximal end and distal port 12. The lumen is adapted for insertion of an ablation catheter having an ablation instrument at its distal end. The lumen may also accommodate other interventional catheters, e.g., an atherectomy catheter. Expandable filtration assembly 20 is mounted on distal region 13 of the catheter. The assembly includes proximal edge 21 circumferentially in contact with an outer surface of the catheter, and distal edge 22 which expands radially outward as depicted in FIG. 6B. The catheter further includes a second lumen 31 communicating with aspiration port 30, and a proximal end which is adapted for attachment to a vacuum. The aspiration port is capable of removing embolic material generated by the ablation instrument under suction.

Figure 7:
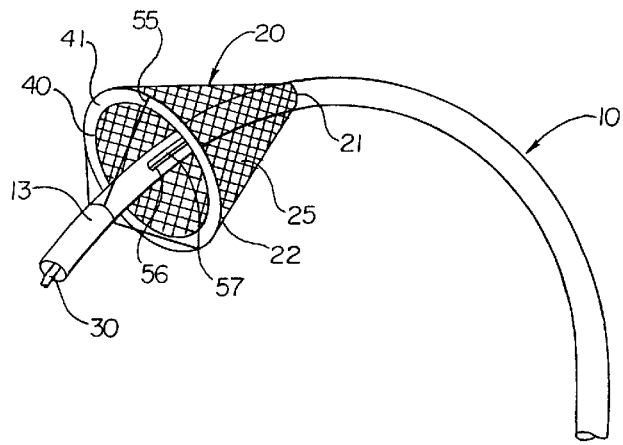
FIG. 7 depicts another embodiment of the guiding catheter system for ablation of ectopic foci having an inflation seal.

In certain embodiments, as depicted in FIG. 7, filtration assembly 20 comprises inflation seal 40 disposed about distal region 13 of the catheter, wherein the inflation seal is expandable between a contracted condition and an enlarged condition. Inflation seal 40 comprises a continuous ring of thin tubing attached to filter mesh 25, which is operably connected to the inflation seal at proximal edge 21 and is closely associated with the outer surface of the catheter at distal edge 22. The inflation seal may be constructed from elastomeric or non-elastomeric tubular material which encloses a donut-shaped chamber 41. When deployed, the inflation seal can be expanded by injecting fluid or gas into chamber 41 to fit tightly against the lumen of a vessel. Chamber 41 is in fluid communication with first tubular passage 56 and second tubular passage 57 which permit chamber 41 to be inflated with gas, or preferably a fluid such as saline. Distal region 13 of the catheter may include a plurality of spokes or folding strings 55 made form Dacron® or other suitable material. Holding strings 55 connect distal region 13 of the catheter to inflation seal 40. The construction and operation of the inflation seal are described in more details in Barbut, et al., U.S. Pat. No. 5,662,671, incorporated herein by reference in its entirety.

Figure 8:
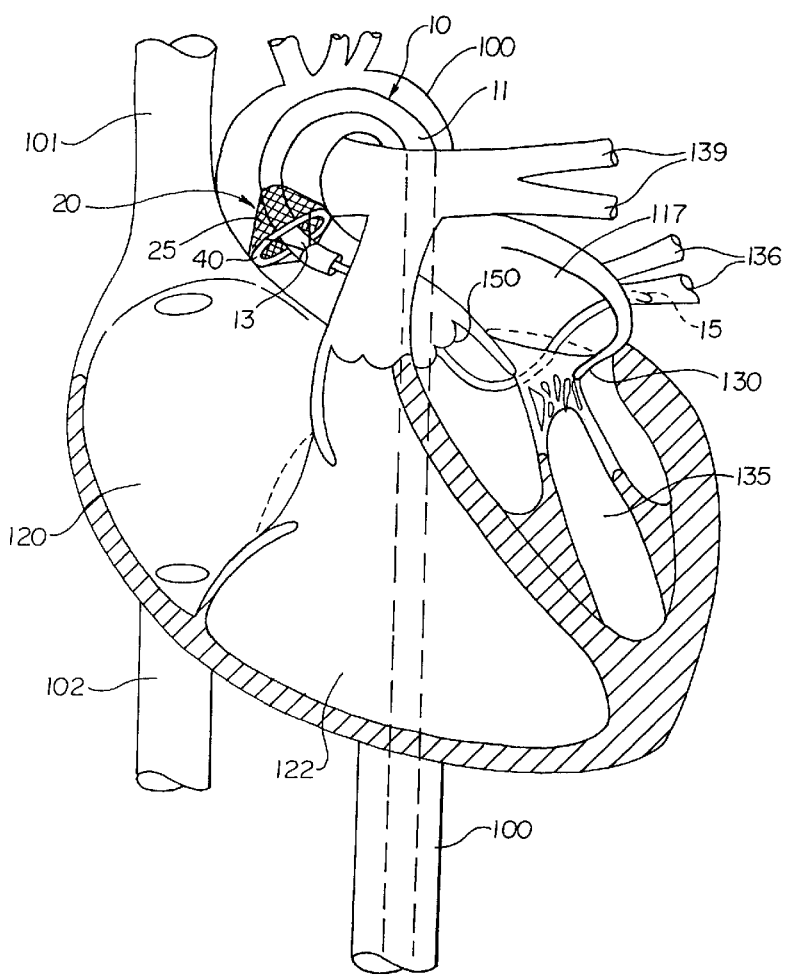
FIG. 8 depicts the catheter system of FIG. 7 inserted in the aorta for ablating the ectopic foci in the pulmonary vein.

In a contracted condition, for example, inflation seal 40 and mesh 25 can be inserted through the femoral artery and up through aorta 100 as depicted in FIG. 8. An ablation catheter having ablation instrument 15 at its distal end is disposed in lumen 11 of the catheter, and is advanced distally through port 30 to position in pulmonary vein 136 after traversing aortic valve 150 and mitral valve 130. Inflation seal 40 is then expanded by injecting fluid or gas into inflation seal 40 to achieve contact with the inner lumen of aorta 100. In this way, embolic material traveling downstream from the pulmonary vein, left atrium 117, and left ventricle 135 during the ablation procedure is captured by filtration assembly 20 positioned in the ascending aorta, thereby preventing movement of the emboli downstream to other organs.

Figure 9A:
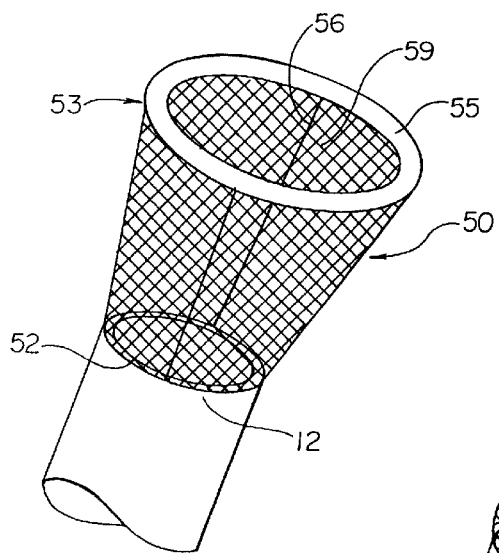
FIG. 9A depicts another embodiment of a trapping mechanism for capturing emboli, having a basket with an adjustable opening at a distal end.
Figure 9B:
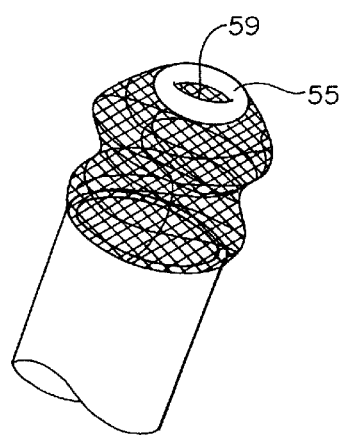
FIG. 9B depicts the trapping mechanism of FIG. 9A in a collapsed condition.

FIGS. 9A and 9B depict an alternative embodiment of the emboli trapping mechanism having basket 50 with an adjustable opening at distal end 12 of the ablation or guiding catheter. In FIG. 9A, basket 50 is attached at seam 52 to distal end 12 of the catheter. Distal region 53 of basket 50 is attached to a contracting loop or inflation member 55 which is secured to the catheter by support wires 56. In use, contracting loop 55 is narrowed as shown in FIG. 9B during catheter insertion, and expanded thereafter to receive embolic material through distal opening 59. After basket 50 receives necrotic tissue or thrombi generated during the ablation procedure, loop 55 is narrowed about the embolic material, which is securely retained by basket 50 and removed when the catheter is withdrawn.

Figure 10A:
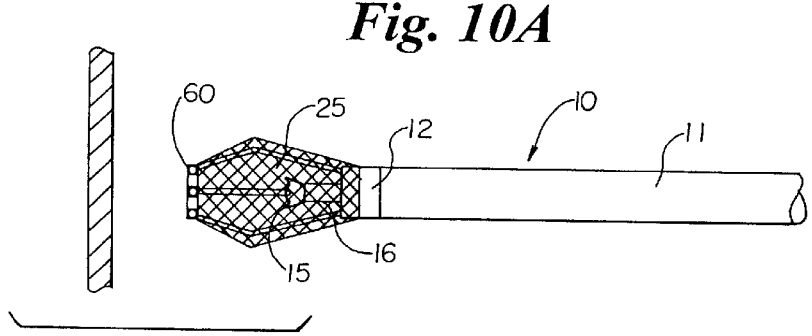
FIG. 10A depicts another embodiment of the trapping mechanism for capturing embolic material, having clamping fingers and associated mesh.
Figure 10B:
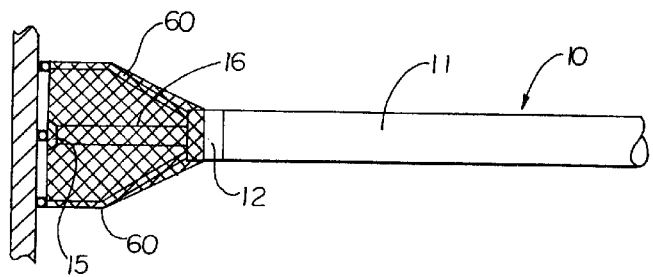
FIG. 10B depicts the trapping mechanism of FIG. 10A in an expanded state.

Another embodiment of the trapping mechanism is depicted in FIGS. 10A and 10B. Distal end 12 of catheter 10 includes a plurality of clamping fingers 60 which are operable between an open and closed condition. Filtration mesh 25 is disposed over fingers 60 and is positioned to capture embolic material dislodged during the ablative procedure. Ablation catheter 16 having ablation instrument 15 at its distal end is moveably inserted in lumen 11 of catheter 10. In certain embodiments, ablation catheter 16 may include an aspiration lumen and distal aspiration port. In use, catheter 10 approaches the ectopic focus with open fingers 60 as shown in FIG. 10B. Ablation instrument 15 is positioned adjacent to the ectopic focus having fingers 60 and mesh 25 closed about the ablation catheter. Embolic material generated during the ablative procedure is captured by mesh 25.

Figure 11:
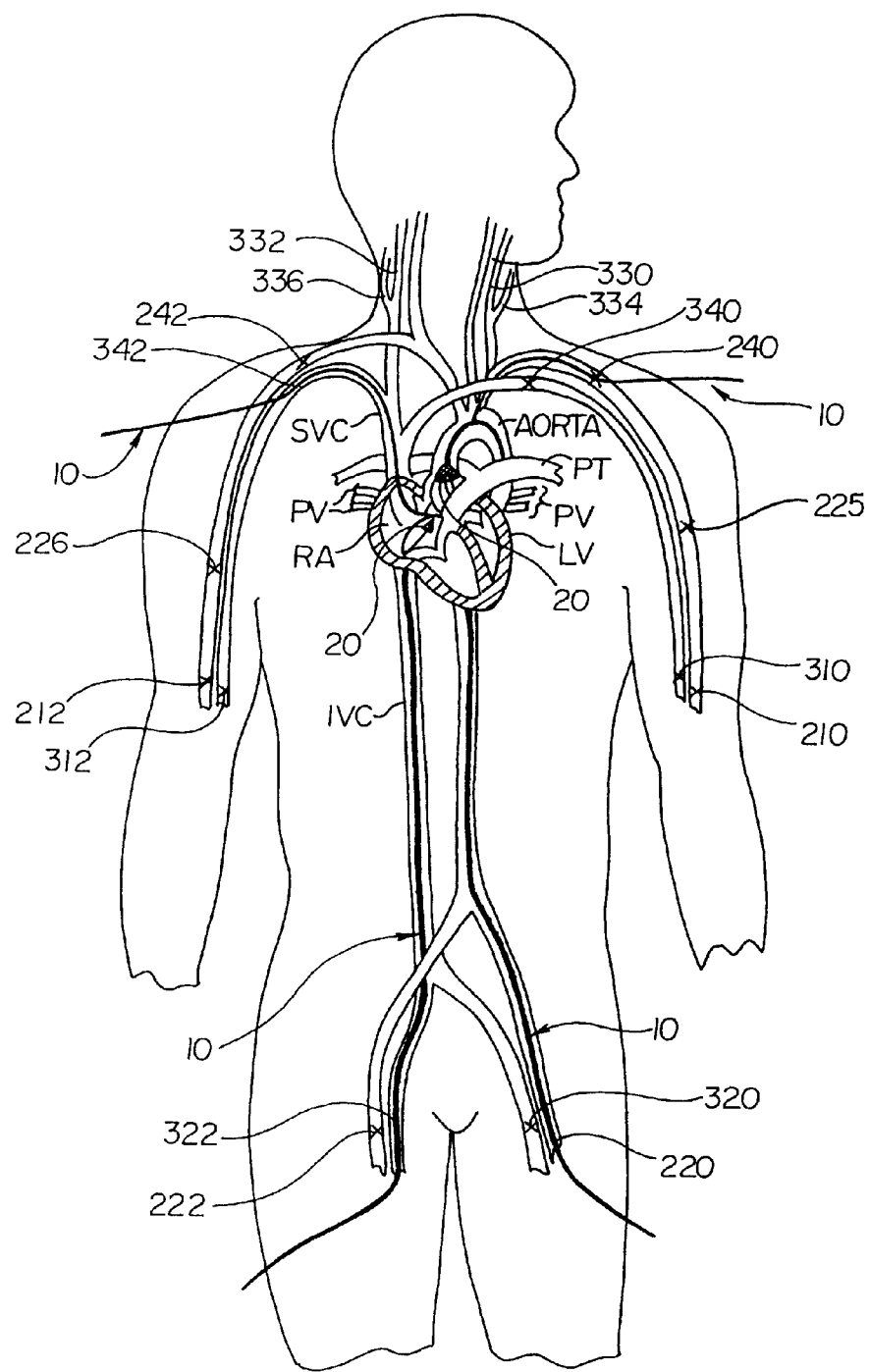
FIG. 11 depicts various entry sites for catheter insertion.

A variety of entry sites available for insertion of the ablation catheter from peripheral arteries and veins into the cardiac chambers or the great vessels are shown in FIG. 11. For ablating ectopic atrial foci located in the right atrial appendage, the ablation catheter 10 can be inserted through right subclavian vein 342, left subclavian vein 340, right internal jugular vein 332, left internal jugular vein 330, right external jugular vein 336, left external jugular vein 334, right median cubital vein 312, or left median cubital vein 310, and through superior vena cava (SVC) to insert in the right atrium (RA). Alternatively, the catheter can be inserted through right femoral vein 322 or left femoral vein 320 and up through the inferior vena cava (IVC) to insert in the RA. FIG. 11 depicts catheter 10 entering the RA through right femoral vein 322 and right subclavian vein 342. Entrapping mechanism 20 is positioned in the RA. For ablating ectopic foci located in the left atrium (LA) or the pulmonary veins (PV), the catheter can be inserted through right brachial artery 212, left brachial artery 210, right axillary artery 226, left axillary artery 225, right subclavian artery 242, or left subclavian artery 240 and through the aorta to enter the LA or the PV. Alternatively, the catheter can be inserted through right femoral artery 222 or the left femoral artery 220, and up through the descending aorta to enter the LA or the PV. FIG. 11 depicts catheter 10 inserted through left femoral artery 220 and left subclavian artery 240. Entrapping mechanism 20 is positioned in the ascending aorta to prevent emboli from traveling downstream in the aorta. Alternatively, ablation of ectopic foci in the LA or the PV can be achieved by a trans-septal approach, having the catheter traversing through the foramen ovale from the RA to the LA. In this approach, the catheter is inserted through the peripheral veins.

The length of catheter will generally be between 10 and 200 centimeters, preferably approximately between 30 and 150 centimeters. The inner diameter of the catheter lumen will generally be between 0.2 and 0.8 centimeters, preferably between approximately 0.3 and 0.5 centimeters. The mesh permits flow rates as high as 3 L/min or more, more preferably 3.5 L/min or more, more preferably 4 L/min or more, more preferably 4.5 L/min or more, more preferably 5 L/min or more, more preferably 5.5 L/min or more, most preferably at 6 L/min or more at pre-filter maximum aortic systolic pressures (proximal to the mesh) of around 200 mmHg or less. The outer diameter of the expanded inflation seal will generally be at least 1 centimeters, more preferably at least 1.5 centimeters, more preferably at least 2 centimeters, more preferably at least 2.5 centimeters, more preferably at least 3 centimeters, more preferably at least 3.5 centimeters, more preferably at least 4 centimeters, more preferably at least 4.5 centimeters, more preferably at least 5 centimeters, more preferably at least 5.5 centimeters, more preferably at least 6 centimeters, more preferably at least 6.5 centimeters, more preferably at least 7 centimeters, more preferably at least 7.5 centimeters, more preferably at least 8 centimeters, more preferably at least 8.5 centimeters, more preferably at least 9 centimeters, more preferably at least 9.5 centimeters, more preferably at least 10 centimeters, more preferably at least 10.5 centimeters, more preferably at least 11 centimeters, more preferably at least 11.5 centimeters, more preferably at least 12.0 centimeters. These ranges cover suitable diameters in the aorta and the pulmonary veins for both pediatric and adult use. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A percutaneous catheter for ablation of ectopic foci, comprising:

an elongate member having a proximal end and a distal end;

an expandable filter mounted on a distal region of the elongate member;

means for ablating ectopic foci disposed at the distal end of the elongate member; and wherein during use, the filter is expanded to capture necrosed tissue particles generated during the ablation.

2. The catheter of claim 1, wherein the means for ablating ectopic foci include a thermal ablation device.

3. The catheter of claim 1, wherein the means for ablating ectopic foci include a laser ablation device.

4. The catheter of claim 1, wherein the means for ablating ectopic foci include a microwave ablation device.

5. The catheter of claim 1, wherein the filter surrounds the ablation instrument.

6. The catheter of claim 1, wherein the filter is disposed proximal the ablation instrument.

7. The catheter of claim 6, wherein the filter has a proximal edge circumferentially in contact with an outer surface of the elongate member, and a distal edge which expands radially outward.

8. The catheter of claim 1, wherein the catheter includes a second lumen communicating with an aspiration port.

9. The catheter of claim 1, wherein the filter may be a basket.

10. A percutaneous guiding catheter system for ablation of ectopic foci, comprising:

an elongate member having a proximal end, a distal end, and a lumen therebetween;

an expandable filter mounted on a distal region of the elongate member; and a catheter comprising means for ablating ectopic foci disposed within the lumen of the elongate member, and having an ablation instrument at its distal end.

11. The catheter of claim 10, wherein the means for ablating ectopic foci include a thermal ablation device.

12. The catheter of claim 10, wherein the means for ablating ectopic foci include a laser ablation device.

13. The catheter of claim 10, wherein the means for ablating ectopic foci include a microwave ablation device.

14. The catheter of claim 10, wherein the ablation instrument extends beyond the distal end of the elongate member.

15. The catheter of claim 10, wherein the catheter includes a second lumen communicating with an aspiration port.

16. The catheter of claim 10, wherein the filter has a proximal edge circumferentially in contact with an outer surface of the elongate member, and a distal edge which expands radially outward.

17. The catheter of claim 10, wherein the proximal end of the catheter is adapted for attachment to a vacuum.

18. The catheter of claim 10, wherein the filter is a basket.

19. A method for ablation of ectopic foci, comprising the steps of:

providing a catheter having a proximal end, a distal end, an ablation instrument at the distal end, and a filter on a distal region of the elongate member;

inserting the catheter into a vessel;

positioning the ablation instrument adjacent the ectopic foci;

expanding the filter; and ablating the ectopic foci, wherein necrosed tissue particles generated during ablation are captured by the filter.

20. The method of claim 19, wherein the ectopic foci are located in the left atrium.

* * * * *